United States Patent [19]

Schubart

[11] 4,223,138

[45] Sep. 16, 1980

[54] PROCESS FOR THE SELECTIVE PREPARATION OF MONOHYDROXYALKYLATED AMINES

[75] Inventor: Rüdiger Schubart, Bergisch Gladbach, Fed. Rep. of Germany

[73] Assignee: Bayer Aktiengesellschaft, Leverkusen, Fed. Rep. of Germany

[21] Appl. No.: 891,562

[22] Filed: Mar. 29, 1978

[30] Foreign Application Priority Data

Apr. 16, 1977 [DE] Fed. Rep. of Germany ....... 2716946

[51] Int. Cl.$^2$ .............................................. C07C 89/02
[52] U.S. Cl. ............................... 544/162; 260/239 A; 260/239 E; 260/239 B; 260/239 BC; 260/239 BF; 260/326.5 R; 260/326.5 G; 260/330; 260/333; 260/563 R; 260/563 C; 260/563 P; 260/573; 260/584 R; 260/584 C; 544/59; 544/170; 544/401; 546/246; 546/248; 546/334; 546/344
[58] Field of Search ........... 260/584 R, 584 C, 563 C, 260/573; 23/263; 544/162; 546/334

[56] References Cited

U.S. PATENT DOCUMENTS

| 2,856,363 | 10/1968 | Brennan ....................... 260/584 R X |
|---|---|---|
| 3,317,505 | 5/1967 | Braus ............................ 260/584 R X |
| 3,328,467 | 6/1967 | Hamilton ...................... 260/584 R X |
| 3,454,647 | 7/1969 | Kersnar et al. ................. 260/584 R |
| 3,872,171 | 3/1975 | Cronin et al. .................... 260/584 R |

FOREIGN PATENT DOCUMENTS 598298  2/1948  United Kingdom ............... 260/584 R

OTHER PUBLICATIONS

B.J.O.S. Final Report, No. 1059, pp. 48–52 (1974).
Narayan et al., "Chem. Ab.", vol. 85, Ab. No. 192775f (1976).
Nordmann et al., "Chem. Ab.", vol. 81, Ab. No. 104978p (1974).
Knorr et al., "Chem. Ber.", vol. 35, pp. 4470–4473 (1902).

*Primary Examiner*—John Doll
*Attorney, Agent, or Firm*—Sprung, Felfe, Horn, Lynch & Kramer

[57] ABSTRACT

A process for the preparation of an aminoethanol is described wherein an amine is vaporized in a collection vessel and the vapors are caused to pass upwardly through a defined reaction zone into a condensation zone where they are condensed and caused to flow downwardly into the reaction zone. In the reaction zone the flow toward the collection zone is retarded and, while retarded, epoxide reactant is directed thereagainst. The aminoethanol so formed is removed into the collection zone such as by directing condensed amine thereagainst.

10 Claims, 3 Drawing Figures

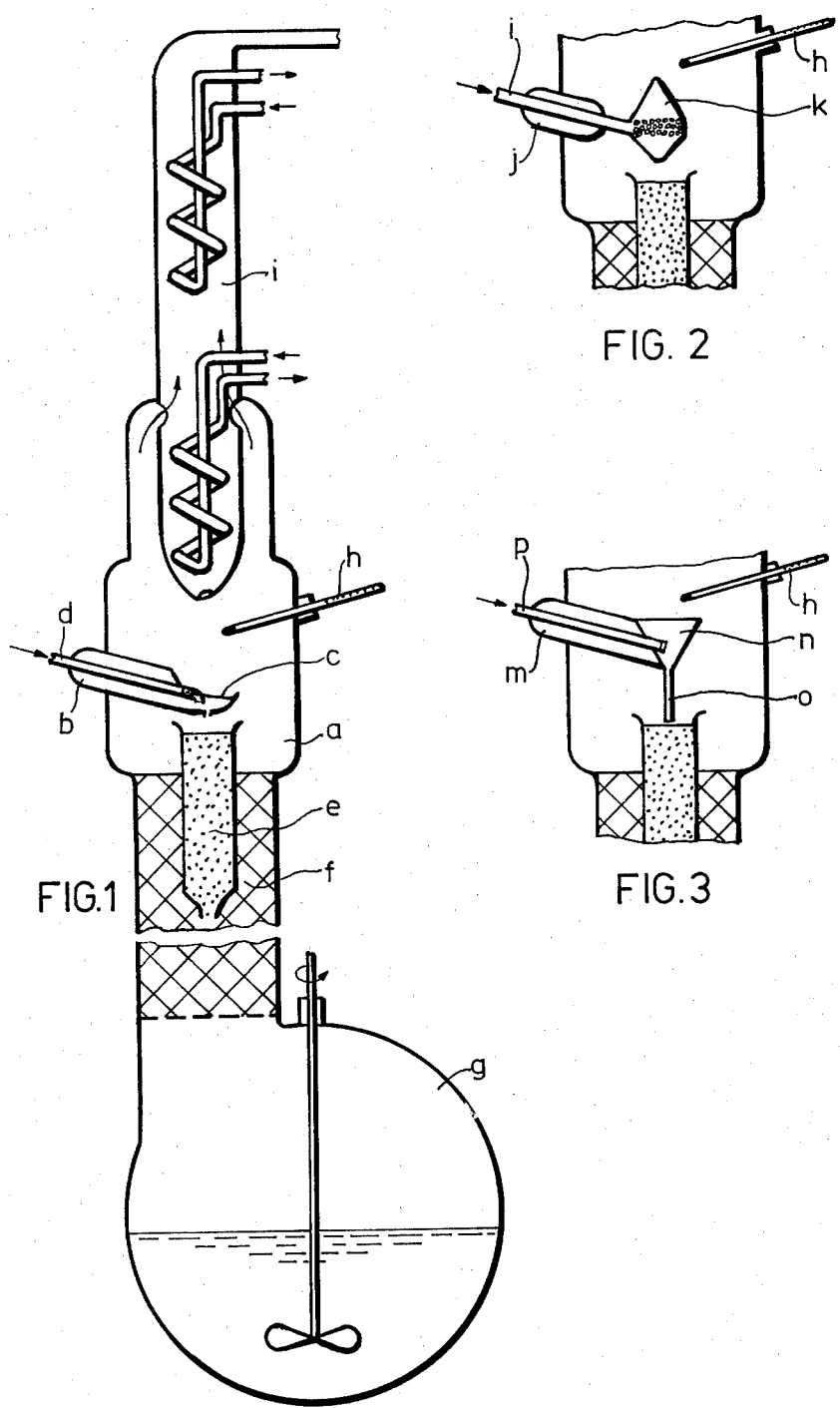

PROCESS FOR THE SELECTIVE PREPARATION OF MONOHYDROXYALKYLATED AMINES

The invention relates to a process for the selective preparation of monohydroxyethylated amines.

It is known to ethoxylate amines by initially introducing the amine into a reaction vessel and carrying out the reaction with ethylene oxide at room temperature or at elevated temperature (Houben-Weyl, Methoden der Organischen Chemie (Methods of Organic Chemistry), XI/1, pages 312 et seq. (1957)). Numerous by-products are formed in the known processes and the yield of monohydroxylated amines is low.

It is also known to employ the amine in excess in the reaction or to add large amounts of diluents, for example water (Chem. Ber. 35, 4470 (1902)).

According to the present invention there is provided a process for the preparation of an aminoethanol comprising vaporising an amine in a vessel which is connected via a tube to a condenser, which condenser includes a reaction zone adjacent the tube and a collector located in the reaction zone above the top end of the tube, condensing the amine vapour so that it drips onto the collector, introducing an epoxide into the reaction zone, reacting the epoxide with condensed amine on the collector, and flushing the reaction product from the collector back into the vessel.

The process according to the invention may be illustrated with the aid of the following equation:

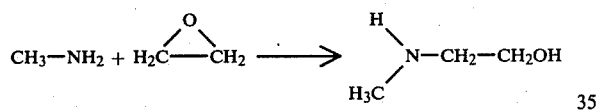

Possible amines for the process according to the invention are primary and secondary amines. Primary and secondary amines for the process according to the invention can be, for example, amines of the formula

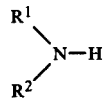

wherein
$R^1$ and $R^2$ are identical or different and denote hydrogen, an optionally substituted, straight-chain, branched or cyclic alkyl or alkylene radical or an optionally substituted aryl radical or, together, form a saturated or unsaturated hydrocarbon ring which optionally also contains, in the ring, nitrogen, oxygen or sulphur.

Amines of the formula

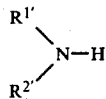

wherein
$R^{1'}$ and $R^{2'}$ are identical or different and denote hydrogen, an optionally substituted, straight-chain or branched $C_1$ to $C_{12}$ alkyl or $C_1$ to $C_{12}$ alkylene radical or an optionally substituted aryl radical or, together, form a saturated or unsaturated hydrocarbon ring or a nitrogen-, oxygen- or sulphur-containing hydrocarbon ring with 3 to 12 ring members,
may be mentioned as being preferred.

Amines of the formula

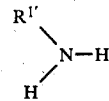

wherein
$R^{1'}$ has the abovementioned meaning,
are particularly preferred.

Epoxides for the process according to the invention can be, for example, epoxides of the formula

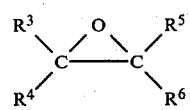

wherein
$R^3$ to $R^6$ are identical or different and denote hydrogen, an optionally substituted, straight-chain, branched or cyclic alkyl or alkylene radical, it being possible for $R^3$ and $R^4$, $R^5$ and $R^6$, $R^3$ and $R^5$, or $R^4$ and $R^6$ to be linked by an alkyl or alkylene radical to form a ring with 5 or 6 carbon atoms, or an optionally substituted aryl radical.

Epoxides of the formula

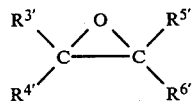

wherein
$R^{3'}$ to $R^{6'}$ are identical or different and denote hydrogen, an optionally substituted, straight-chain or branched $C_1$ to $C_{12}$ alkyl or $C_5$ to $C_{12}$ cycloalkyl or $C_1$ to $C_{12}$ alkenyl radical or an optionally substituted aryl radical,
may be mentioned as being preferred.

Ethylene oxide is particularly preferred.

Straight-chain or branched alkyl radicals ($R^1$ to $R^6$) which may be mentioned are hydrocarbon radicals with 1 to 18, preferably 1 to 12, carbon atoms, such as methyl, ethyl, propyl, isopropyl, butyl, isobutyl, pentyl, isopentyl, hexyl and isohexyl.

Cycloalkyl radicals which may be mentioned are cyclic hydrocarbon radicals with 4 to 12, preferably 5 to 8, carbon atoms, such as cyclopentyl, cyclohexyl, cycloheptyl and cyclooctyl.

Straight-chain or branched alkenyl radicals which may be mentioned are unsaturated hydrocarbon radicals with 2 to 18, preferably 2 to 12, carbon atoms, such as ethenyl, propenyl, isopropenyl, butenyl, isobutenyl, pentenyl, isopentenyl, hexenyl and isohexenyl.

Cycloalkenyl radicals which may be mentioned are cyclic monounsaturated or polyunsaturated hydrocarbon radicals with 4 to 12, preferably 5 to 7, carbon atoms, such as cyclopentenyl, cyclopentadienyl, cyclohexenyl, cyclohexadienyl, cycloheptenyl and cycloheptadienyl.

Aryl radicals ($R^1$ to $R^6$) which may be mentioned are aromatic hydrocarbon radicals with 6 to 14 carbon atoms, preferably phenyl, naphthyl and anthranyl.

Saturated cyclic amines which are formed by linking the radicals $R^1$ and $R^2$ can have 3 to 12 ring members. Examples which may be mentioned are: aziridine, azetidine, pyrrolidine, piperidine, hexamethyleneimine, heptamethyleneimine, octamethyleneimine, nonamethyleneimine, decamethyleneimine and undecamethyleneimine.

Unsaturated cyclic amines which are formed by linking the radicals $R^1$ and $R^2$ can have 3 to 12 ring members. Examples which may be mentioned are: pyrroline, tetrahydropyridine, 1,4-dihydropyridine, dihydroazepine and tetrahydroazepine.

Nitrogen-, oxygen- or sulphur-containing cyclic amines which are formed by linking the radicals $R^1$ and $R^2$ can have 3 to 12 ring members. Examples which may be mentioned are: piperazine, morpholine, thiomorpholine, di-aza-cycloheptane, oxa-aza-cycloheptane, thia-aza-cycloheptane, di-aza-cyclooctane, oxa-aza-cyclooctane, oxa-aza-cyclooctane, oxa-thia-aza-cyclooctane, di-aza-cyclononane, oxa-aza-cyclononane, di-aza-cyclodecane, oxa-aza-cyclodecane, di-aza-cycloundecane, oxa-aza-cycloundecane, di-aza-cyclododecane and oxa-aza-cyclododecane.

Possible substituents of the radicals $R^1$ to $R^6$ are all the substituents which are not altered under the reaction conditions. Examples which may be mentioned are: methyl, ethyl, propyl, isopropyl, butyl, isobutyl, pentyl, isopentyl, hexyl, isohexyl, cyclohexyl, vinyl, isopropenyl and phenyl.

The following amines may be mentioned as examples of amines for the process according to the invention: ammonia, methylamine, ethylamine, propylamine, butylamine, pentylamine, hexylamine, heptylamine, octylamine, nonylamine, decylamine, undecylamine, dodecylamine, cyclopentylamine, cyclohexylamine, methylcyclohexylamine, aniline, toluidine, ethanolamine, ethylenediamine, 1,2-propylenediamine, 1,3-propylenediamine, 1,4-butylenediamine, 1,6-diaminohexane, 1,4-diaminocyclohexane, diethylenetriamine and 1,5-diamino-3-oxapentane.

The following epoxides may be mentioned as examples of epoxides for the process according to the invention: ethylene oxide, propylene oxide, 1-butylene oxide, cis-2-butylene oxide, isobutylene oxide, trans-2-butylene oxide, 1-pentylene oxide, 2-pentylene oxide, hexylene oxide, heptylene oxide, octylene oxide, nonylene oxide, decylene oxide, undecylene oxide, 1-diisobutylene oxide, 2-diisobutylene oxide, tripropylene oxide, cyclohexene oxide, cyclopentene oxide, cycloheptene oxide, cyclooctene oxide, cyclododecane oxide, methyl-cyclohexene oxide, cyclohexadiene monoepoxide, cyclopentadiene monoepoxide, vinyloxirane, isoprene oxide, chloroprene oxide, styrene oxide and α-methylstyrene oxide.

Examples of suitable collectors are, for example, constrictions of the reaction space which cause the epoxide and the amine to come into contact for a short time. The time should be calculated such that the desired reaction proceeds to completion and, because of the very low residence time of all the reactants with one another, secondary reactions are virtually impossible and thus virtually no by-products are obtained.

A constriction of the reaction space can be, for example, in the form of a device which is let into the reaction space and has, on the part located in the reaction space, a concave depression into which the gaseous epoxide is fed into the liquid phase therein through a feed line, which appropriately ends with a frit, and is then reacted. In addition, it can be in the form of a hollow cone with a porous annular zone through which the gaseous epoxide is fed into the thin liquid film running over the cone and is reacted directly.

It is also possible for the constriction for the process according to the invention to be in the form of a narrowing of the reaction space to give a tube, the upper part of which is in the form of a funnel and contains the gas inlet through which the gaseous epoxide is directly passed, by means of a tube which is approximately provided with a frit, into the hot liquid amine, which has accummulated somewhat, refluxing from the condenser and is rapidly reacted.

The reflux ratio of gaseous epoxide/liquid amine for the process according to the invention is regulated so that less than the molar amount of epoxide is present and it is used up by the reaction completely, immediately after emerging through the gas inlet. In general, the process according to the invention is carried out with a reflux ratio of 1 to 20 mols, preferably of 1 to 10 mols, of amine per mol of epoxide.

The choice of the most favourable constriction of the reaction space depends on the required contact time of the reactants. If the contact time is very short, a device let into the reaction space is preferred which is in the form of a cone. For longer reaction times it can be advantageous to use devices in which the part let into the reaction space is in the form of a depression.

The separation of the reaction mixture from the rising vapour of the amine by means of a tube let into the column is a further characteristic of the process according to the invention. Examples of columns which may be mentioned are Vigreux columns, packed columns and bubble tray columns. In general, the tube let into the column can be packed with the same material as the surrounding column.

An embodiment of the process according to the invention may be illustrated with the aid of FIGS. 1, 2 and 3 of the accompanying drawings which represent possible apparatuses for the process The liquid amine, optionally in the presence of 0.01 to 35%, preferably 5 to 15%, of water, is heated to the boil in a flask (g). The amine, in the form of a vapour, rises through the column (f) and the reaction space (a) to the condenser (i) and is condensed there. In the case of FIG. 1, this condensate of the amine runs onto the concave depression (c) of the device (b) let into the reaction space. In the case of Diagram 2, the amine drips onto the tip of the cone (k) of the device (j) let into the reaction space. In the case of Diagram 3, the amine runs into the funnel (n), which is in the form of a tube (o) at the lower end, of the device (m) let into the reaction space.

The epoxide, which can optionally be diluted with an inert gas, such as nitrogen or argon, is introduced through the gas inlet (d, l or p) of the devices (b, j or m) let into the reaction space and reacts with the amine in the depression (c) or on the cone (k) or in the tube (o).

The aminoethanol formed is flushed out of the reaction space (a) by further amine subsequently running from the condenser (i).

The mixture which runs off, which essentially consists of the aminoethanol formed and unreacted amine, flows through the tube (e) let into the column (f) and is thus, separated from the rising vapour of the amine, passed downwards. The mixture then flows further into the flask (g), from which the amine is again vaporised. Since the aminoethanol as a rule has a higher boiling point than the amine it remains in the flask and can be isolated in the customary manner, for example by distillation, after the reaction has ended.

The process according to the invention can also be carried out continuously, the starting materials being fed into the upper part of the apparatus and the end product being removed from the vaporiser.

It is also possible to locate the reaction space outside the tube which is mounted on the vaporising vessel; in this case, the condensed amine is passed into the external reaction space for the reaction and then, after the reaction, is passed into the lower part of the tube, which is in the form of a column.

Virtually all the customary materials, such as glass, quartz or steel, can be used for the manufacture of the apparatus for the process according to the invention.

The process according to the invention can be carried out under reduced, normal or elevated pressure. By changing the pressure it is easily possible to employ a component in the most advantageous state of aggregation.

Aminoethanols of the formula

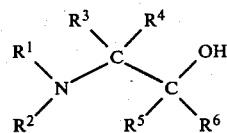

VI wherein
$R^1$ to $R^6$ have the abovementioned meaning,
can be prepared by the process according to the invention. In particular, it is possible to prepare compounds of the formula

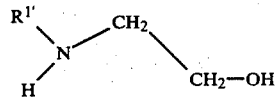

VII wherein
$R^{1'}$ has the abovementioned meaning.

In addition, the preparation of compounds of the formula

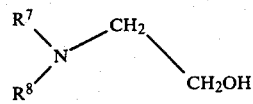

VIII wherein
$R^7$ and $R^8$ are identical or different and denote an optionally substituted straight-chain or branched $C_1$ to $C_{12}$ alkyl, $C_5$ to $C_{12}$ cycloalkyl or $C_2$ to $C_{12}$ alkenyl radical or an optionally substituted aryl radical,
is also preferred.

Furthermore, the preparation of compounds of the formula

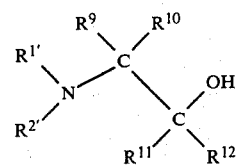

IX wherein
$R^{1'}$ and $R^{2'}$ have the abovementioned meaning and $R^9$ to $R^{12}$ are identical or different and denote an optionally substituted, straight-chain or branched $C_1$ to $C_{12}$ alkyl, $C_5$ to $C_{12}$ cycloalkyl or $C_2$ to $C_{12}$ alkenyl radical or an optionally substituted aryl radical,
is preferred.

The following aminoethanols may be mentioned as examples: N-methylaminoethanol, N-ethylaminoethanol, N-propylaminoethanol, N-isopropylaminoethanol, N-butylaminoethanol, N-iso-butylaminoethanol, N-sec.-butylaminoethanol, N-tert.-butylaminoethanol, N-pentylaminoethanol, N-iso-pentylaminoethanol, N-sec.-pentylaminoethanol, N-tert.-pentylaminoethanol, N-hexylaminoethanol, N-sec.-hexylaminoethanol, N-tert.-hexylaminoethanol, N-iso-hexylaminoethanol, N-heptylaminoethanol, N-iso-heptylaminoethanol, N-sec.-heptylaminoethanol, N-tert.-heptyl-aminoethanol, N-octylaminoethanol, N-iso-octylaminoethanol, N-sec.-octylaminoethanol, N-tert.-octylaminoethanol, N-diisobutylaminoethanol, N-(2-ethylhexyl)-aminoethanol, N-iso-nonylaminoethanol, N-sec.-nonylaminoethanol, N-tert.-nonylaminoethanol, N-decylaminoethanol, N-sec.-decylaminoethanol, N-tert.-decylaminoethanol, N-undecylaminoethanol, N-dodecylaminoethanol, N-di-tert.-dodecylaminoethanol, N-tridecylaminoethanol, N-tetradecylaminoethanol, N-pentadecylaminoethanol, N-hexadecylaminoethanol, N-heptadecylaminoethanol, N-octadecylaminoethanol, N-cyclohexylaminoethanol, N-cyclopentylaminoethanol, N-cycloheptylaminoethanol, N-cyclooctylaminoethanol, N-cyclononylaminoethanol, N-(methylcyclohexyl)-aminoethanol, N-(cyclohexylmethyl)-aminoethanol, N-(cyclohexenyl)-aminoethanol, N-(cyclohexenylmethyl)-aminoethanol, N-phenylaminoethanol, N-(2-methylphenyl)-aminoethanol, N-(3-methylphenyl)-aminoethanol, N-(4-methylphenyl)-aminoethanol, N-(2-ethylphenyl)-aminoethanol, N-(4-ethylphenyl)-aminoethanol, N-(2-propylphenyl)-aminoethanol, N-(4-propylphenyl)-aminoethanol, N-(2,3-dimethylphenyl)-aminoethanol, N-(3,4-dimethylphenyl)-aminoethanol, N-(2,4-dimethylphenyl)-aminoethanol, N-(2,6-dimethylphenyl)-aminoethanol, N-(2,5-dimethylphenyl)-aminoethanol, N-(methoxyethyl)-aminoethanol, N-(ethoxyethyl)-aminoethanol, N-(propoxyethyl)-aminoethanol, N-(butoxyethyl)-aminoethanol, N-(methoxypropyl)-aminoethanol, N-(ethoxypropyl)-aminoethanol N-(propoxypropyl)-aminoethanol, N-(isopropoxypropyl)-aminoethanol, N-(butoxypropyl)-aminoethanol, N-(pentoxypropyl)-aminoethanol, N-(hexoxypropyl)-aminoethanol, N-(heptoxypropyl)-aminoethanol, N-(sec.-butoxypropyl)-aminoethanol, N-(tert.-butoxypropyl)-aminoethanol, N-(isobutoxypropyl)-aminoethanol, N-(iso-pentoxypropyl)-aminoethanol, N-(octyloxypropyl)-aminoethanol, N-(2-ethylhexyloxypropyl)-aminoethanol, N-(methylthioethyl)-aminoethanol, N-(ethylthioethyl)-aminoethanol, N-(propylthioethyl)-aminoethanol, N-(butylthioethyl)- aminoethanol, N-(pentylthioethyl)-aminoethanol, N-(methylthiopropyl)-aminoethanol, N-(ethylthiopropyl)-aminoethanol, N-(propylthiopropyl)-aminoethanol, N-butyl-thiopropyl)-aminoethanol, N-(phenylthiopropyl)-aminoethanol, N-(dimethylaminoethyl)-aminoethanol, N-(diethylaminoethyl)-aminoethanol, N-(dipropylaminoethyl)-aminoethanol, N-(dimethylaminopropyl)-aminoethanol, N-(diethylaminopropyl)-aminoethanol, N-(dipropylaminopropyl)-aminoethanol, N-(dibutylaminopropyl)-aminoethanol, N-(N'-methylcyclohexylaminopropyl)-aminoethanol, N-(cyclohexylaminopropyl)-aminoethanol, N-(N'-methylallylaminopropyl)-aminoethanol, N-(diallylaminopropyl)-aminoethanol, N-(N'-morpholinopropyl)-aminoethanol, N-(N'-piperidinopropyl)-aminoethanol, N-(N'-pyrrolidinopropyl)-aminoethanol, N-(aminoethyl)-aminoethanol, N-(aminopropyl)-aminoethanol, N-(aminopropyl)-aminoethanol, N-piperazino-ethanol, N-(2-methylpiperazino)-ethanol, N-(2,6-dimethylpiperazino)-ethanol, N-morpholino-ethanol, N-piperidinoethanol, N-(N'-methylpiperazino)-ethanol, piperidino-4-aminoethanol, 2,2,6,6-tetramethyl-piperidino-4-aminoethanol, N-[(N'-aminoethyl)-aminoethyl]-aminoethanol, N-[(N'-aminopropyl)-aminoethyl]-aminoethanol, N-(amino-tert.-butyl)-aminoethanol, N-(amino-butyl)-aminoethanol, N-(amino-sec.-butyl)-aminoethanol, N-(amino-pentyl)-aminoethanol, N-(amino-hexyl)-aminoethanol, N-(hydroxyethylamino)-ethanol, N-(2-hydroxypropyl)-aminoethanol, N-(3-hydroxypropyl)-aminoethanol, N-(amino-ethyl)-aminopropanol, N-(amino-ethyl)-amino-(1,2-dimethyl)-ethanol, N-(amino-ethyl)-amino-(2-ethyl)-ethanol, N-(amino-ethyl)-amino-(1-ethyl)-ethanol, N-(amino-ethyl)-amino-(1,1-dimethyl)-ethanol, N-(amino-ethyl)-amino-(1-propenyl)-ethanol, N-(amino-ethyl)-amino-(1-vinyl)-ethanol, N-(aminoethyl)-amino-(2-vinyl)-ethanol, N-(amino-ethyl)-amino-(2-phenyl)-ethanol, N-(amino-propyl)-amino-(1-vinyl)-ethanol, N-(aminoethyl)-amino-(1-cyclohexyl)-ethanol, N-(aminopropyl)-aminopropanol, N-(amino-propyl)-amino-(2-vinyl)-ethanol, N-(trimethylcyclohexyl)-aminoethanol, 2-(amino-ethyl)-aminocyclohexanol, 2-(amino-ethyl)-amino-cyclopentanol, N-(N'-hydroxyethylaminoethyl)-aminoethanol, 2-(amino-propyl)-aminocyclohexanol, N-[(N'-amino-propyl)-aminopropyl]-aminoethanol, 2-amino-propyl)-amino-cyclopentanol, 4-(N'-methyl-piperidino)-aminoethanol, N-[(N'-(2-amino-propyl)-aminopropyl)]-aminoethanol, 4-(N-methyl)-2,2,6,6-tetramethyl-piperidino-ethanol, 1-vinyl-aminoethanol and 2-vinyl-aminoethanol.

The following new aminoethanols can be prepared by the process according to the invention: 2-[(3-dimethylaminopropyl)-amino-]-ethanol, 2-[(3,5,5-trimethylcyclohexyl)-amino-]ethanol and 2-{[3-(2-ethylhexyloxy)-propyl-]-amino}-ethanol.

The aminoethanols which can be prepared by the process according to the invention can be used as intermediate products for the preparation of vulcanisation accelerators (U.S. Pat. No. 2,273,424, U.S. Pat. No. 3,215,703 and U.S. Pat. No. 3,370,051). The aminoethanols themselves can be used as light stabilisers. The new aminoethanols are particularly suitable for these fields of application.

It is surprising that aminoethanols can be prepared with higher selectivity by the process according to the invention. This is particularly surprising since it is known that it is not possible to steer, for example, the reaction of ammonia and ethylene oxide so that the monohydroxyethylated, dihydroxyethylated and trihydroxyethylated product is formed even with varying proportions of starting materials (BIOS Final Report 1,059 (1974)). In addition, formation of amino-polyethers frequently occurs.

EXAMPLES

A. Reaction apparatus

The reaction apparatus represented in Diagram 1 is used in the examples which follow.

The apparatus consists of a vaporising vessel (g) which contains the amine. A column (f) filled with packing, into which an empty tube (e) which narrows towards the bottom is let, is mounted on the vaporising vessel (g). Above the column (f) is the reaction space (a) into which a device (b) is let, of which the part located in the reaction space is in the form of a concave depression (c).

The epoxide is fed to the depression (c) from outside through the inlet (d) into the device (b).

In addition, the thermometer (h) is let into the reaction space (a) in order to monitor the reaction temperature.

The condenser (i) is arranged above the reaction space such that the liquid component condensed here can run into the depression (c).

B. Reaction of amines with epoxides in the reaction apparatus according to A

EXAMPLE 1

600 g of ethylenediamine and 30 g of water are heated to the boil in the vaporising vessel and are reacted in the reaction space with ~440 g of ethylene oxide at 100° to 120° C.

After the reaction has ended, the reaction mixture, which is in the vaporising vessel, is subjected to fractional distillation. 943 g of hydroxyethylethylenediamine (which corresponds to a yield of 94% of the theoretical conversion) are obtained at boiling point 16/136° to 139° C.

Purity: 99.53%; refractive index: $n_D^{20}$:1.4865

Taking into consideration the unreacted ethlenediamine, this gives a yield of 96% of the theoretical conversion.

EXAMPLES 2 to 19:

The Examples 2 to 19 listed in the table which follows are carried out analogously to Example 1 in the presence of about 5% of water.

Table of the compounds prepared:

| Ex. No. | Starting material | Epoxide | End product | Yield | Melting point or $n_D^{20}$ |
|---|---|---|---|---|---|
| 2 | H₂N~~~N(CH₃)CH₃ | ethylene oxide | HO~~~N(H)~~~N(CH₃)CH₃ | 60% | $n_D^{20}$ 1.4627 |

-continued

Table of the compounds prepared:

| Ex. No. | Starting material | Epoxide | End product | Yield | Melting point or $n_D^{20}$ |
|---|---|---|---|---|---|
| 3 | $H_2N\!-\!\!-\!\!-\!O\!-\!\!-\!\!-\!CH(C_2H_5)\!-\!C_3H_7$ | ethylene oxide | $HO\!-\!\!-\!NH\!-\!\!-\!O\!-\!\!-\!CH(C_2H_5)\!-\!C_3H_7$ | 40% | $n_D^{20}$ 1.4552 |
| 4 | $H_2N\!-\!\!-\!NH\!-\!\!-\!OH$ | ethylene oxide | $HO\!-\!\!-\!N(H)\!-\!\!-\!N(H)\!-\!\!-\!OH$ + $H_2N\!-\!\!-\!N(CH_2CH_2OH)_2$ | 91% | Melting point 87° to 90° C. |
| 5 | $H_2N\!-\!CH(CH_3)\!-\!NH_2$ | ethylene oxide | $HO\!-\!\!-\!NH\!-\!CH(CH_3)\!-\!NH_2$ + $HO\!-\!\!-\!NH\!-\!C(CH_3)(H)\!-\!CH_2NH_2$ | 96% | $n_D^{20}$ 1.4789 |
| 6 | $H_2N\!-\!\!-\!NH\!-\!\!-\!NH_2$ | ethylene oxide | $HO\!-\!\!-\!NH\!-\!\!-\!NH\!-\!\!-\!NH_2$ + $H_2N\!-\!\!-\!N(CH_2CH_2NH_2)(CH_2CH_2OH)$ | 88% | $n_D^{20}$ 1.4995 |
| 7 | $CH_3N\!-\!\!-\!NH$ (piperazine ring) | ethylene oxide | $CH_3N\!-\!\!-\!N\!-\!\!-\!OH$ (piperazine ring) | 91% | $n_D^{20}$ 1.4861 |
| 8 | $H_2N\!-\!C(CH_3)_2\!-\!NH_2$ (with CH₂NH₂) | ethylene oxide | $H_2N\!-\!C(CH_3)_2\!-\!CH_2\!-\!NH\!-\!OH$ + $HO\!-\!\!-\!N(H)\!-\!C(CH_3)_2\!-\!CH_2NH_2$ | 95% | $n_D^{20}$ 1.4733 |
| 9 | $H_2N\!-\!\!-\!OH$ | ethylene oxide | $HO\!-\!\!-\!NH\!-\!\!-\!OH$ | 88% | $n_D^{20}$ 1.4765 |
| 10 | $C_5H_{11}\!-\!NH_2$ | ethylene oxide | $C_5H_{11}\!-\!NH\!-\!\!-\!OH$ | 93% | $n_D^{20}$ 1.4551 |
| 11 | cyclohexyl-$NH_2$ | ethylene oxide | cyclohexyl-$NH\!-\!\!-\!OH$ | 94% | $n_D^{20}$ 1.4865 |
| 12 | $H_2N\!-\!\!-\!NH_2$ | 1-butene oxide | $H_2N\!-\!\!-\!NH\!-\!CH(C_2H_5)\!-\!CH_2OH$ | 90% | $n_D^{20}$ 1.4750 |
| 13 | $H_2N\!-\!\!-\!NH_2$ | 2-butene oxide | $H_2N\!-\!\!-\!NH\!-\!CH(CH_3)\!-\!CH(OH)\!-\!CH_3$ | 95% | $n_D^{20}$ 1.4747 |
| 14 | $H_2N\!-\!\!-\!NH_2$ | propylene oxide | $H_2N\!-\!\!-\!NH\!-\!CH_2\!-\!CH(OH)\!-\!CH_3$ | 90% | $n_D^{20}$ 1.4762 |
| 15 | $H_2N\!-\!(CH_2)_4\!-\!NH_2$ | ethylene oxide | $H_2N\!-\!(CH_2)_4\!-\!NH\!-\!\!-\!OH$ | 90% | $n_D^{20}$ 1.4831 |
| 16 | $H_2N\!-\!CH(CH_3)\!-\!NH_2$ | propylene oxide | $H_2N\!-\!CH(CH_3)\!-\!NH\!-\!CH_2\!-\!CH(OH)\!-\!CH_3$ + isomer | 94% | $n_D^{20}$ 1.4682 |

-continued

Table of the compounds prepared:

| Ex. No. | Starting material | Epoxide | End product | Yield | Melting point or $n_D^{20}$ |
|---|---|---|---|---|---|
| 17 | $H_5C_2\text{—O—}\sim\text{—}NH_2$ | ethylene oxide | $H_5C_2\text{—O—}\sim\text{—}NH\sim OH$ | 91% | Melting point 99° to 100° C. |
| 18 | 2,2,6,6-tetramethylpiperidine (NH$_2$ at 4-position) | ethylene oxide | 4-(2-hydroxyethylamino)-2,2,6,6-tetramethylpiperidine | 91% | Melting point 90° to 100° C. |
| 19 | 3,3,5-trimethyl-5-aminocyclohexane | ethylene oxide | 3,3,5-trimethyl-5-(2-hydroxyethylamino)cyclohexane | 95% | $n_D^{20}$ 1.4755 |

What is claimed is:

1. In a process for the selective preparation of a monohydroxyalkylated amine by reacting an amine with an epoxide, the improvement which comprises vaporizing said amine in a collection vessel and causing the vapors thereof to pass upwardly through a defined reaction zone into a condensation zone, condensing said amine vapors in said condensation zone and causing liquid amine in said condensation zone to pass downwardly into said defined reaction zone and toward said collection zone, retarding the passage of said liquid amine through said defined reaction zone, directing epoxide against the retarded amine and passing the thus-formed aminoethanol into said collection vessel by directing condensed amine thereagainst.

2. A process according to claim 1 wherein the condensed amine is retarded by collecting the same in a concave depression.

3. A process according to claim 1 wherein the condensed amine is retarded by being passed over an upwardly directed cone.

4. A process according to claim 1 wherein the condensed amine is retarded by passing the same over the internal walls of a funnel.

5. A process according to claim 1 wherein the aminoethanol so-formed is flushed from said defined reaction zone by said condensed amine into a tube which feeds said collection vessel whereby the downwardly falling aminoethanol is in out of contact relationship with rising vaporized amine from said collection vessel.

6. A process according to claim 1 wherein the reaction is carried out in the presence of 0.01 to 35 percent by weight water.

7. A process according to claim 1 wherein said amine is a primary or secondary amine and said amine has the formula $$\begin{array}{c} R^1 \\ \phantom{R^1}\diagdown \\ \phantom{R^1}\phantom{\diagdown}N\text{—H} \\ \phantom{R^1}\diagup \\ R^2 \end{array}$$

wherein
R$^1$ and R$^2$ are identical or different and denote hydrogen, an optionally substituted, straight-chain, branched or cyclic alkyl or alkylene radical or an optionally substituted aryl radical or, together, form a saturated or unsaturated hydrocarbon ring which optionally also contains, in the ring, nitrogen, oxygen or sulfur.

8. A process according to claim 1 wherein said amine has the formula $$\begin{array}{c} R^{1'} \\ \phantom{R^{1'}}\diagdown \\ \phantom{R^{1'}}\phantom{\diagdown}N\text{—H} \\ \phantom{R^{1'}}\diagup \\ R^{2'} \end{array}$$

wherein
R$^{1'}$ and R$^{2'}$ are identical or different and denote hydrogen, an optionally substituted, straight-chain or branched C$_1$ to C$_{12}$ alkyl or C$_1$ to C$_{12}$ alkylene radical or an optionally substituted aryl radical or, together, form a saturated or unsaturated hydrocarbon ring or a nitrogen-, oxygen- or sulfur-containing hydrocarbon ring with 3 to 12 ring members.

9. A process according to claim 7 wherein the epoxide has the formula $$\begin{array}{c} R^3 \phantom{xx} O \phantom{xx} R^5 \\ \phantom{R^3}\diagdown\phantom{x}\diagdown\phantom{x}\diagup \\ \phantom{xxx}C\text{————}C \\ \phantom{xxx}\diagup\phantom{xxxxxx}\diagdown \\ R^4 \phantom{xxxxxxxx} R^6 \end{array}$$

wherein
R$^3$ to R$^6$ are identical or different and denote hydrogen, an optionally substituted, straight-chain, branched or cyclic alkyl or alkylene radical, it being possible for R$^3$ and R$^4$, R$^5$ and R$^6$, R$^3$ and R$^5$, or R$^4$ and R$^6$ to be linked by an alkyl or alkylene radical to form a ring with 5 or 6 carbon atoms, or an optionally substituted aryl radical.

10. A process according to claim 7 wherein the epoxide has the formula $$\begin{array}{c} R^{3'} \phantom{xx} O \phantom{xx} R^{5'} \\ \phantom{R^{3'}}\diagdown\phantom{x}\diagdown\phantom{x}\diagup \\ \phantom{xxx}C\text{————}C \\ \phantom{xxx}\diagup\phantom{xxxxxx}\diagdown \\ R^{4'} \phantom{xxxxxxxx} R^{6'} \end{array}$$

wherein
R$^{3'}$ and R$^{6'}$ are identical or different and denote hydrogen, an optionally substituted, straight-chain or branched C$_1$ to C$_{12}$ alkyl or C$_5$ to C$_{12}$ cycloalkyl or C$_1$ to C$_{12}$ alkenyl radical or an optionally substituted aryl radical.

* * * * *

UNITED STATES PATENT AND TRADEMARK OFFICE
CERTIFICATE OF CORRECTION

PATENT NO. : 4,223,138
DATED : September 16, 1980
INVENTOR(S) : RÜDIGER SCHUBART It is certified that error appears in the above—identified patent and that said Letters Patent is hereby corrected as shown below:

In column 12, the melting point for Example 18 should be

--99° to 100°C--

Signed and Sealed this

Thirteenth Day of January 1981

[SEAL]

Attest:

Attesting Officer

SIDNEY A. DIAMOND

Commissioner of Patents and Trademarks